(12) United States Patent
Stoltze et al.

(10) Patent No.: US 8,685,075 B2
(45) Date of Patent: *Apr. 1, 2014

(54) CATHETER WITH STENT AND METHOD FOR THE PRODUCTION OF A CATHETER WITH STENT

(75) Inventors: Jacob Stoltze, Copenhagen V. (DK); Jorgen Kamstrup-Larsen, Allerod (DK)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1606 days.

This patent is subject to a terminal disclaimer.

(21) Appl. No.: 11/541,792

(22) Filed: Oct. 2, 2006

(65) Prior Publication Data

US 2007/0083254 A1 Apr. 12, 2007

Related U.S. Application Data

(63) Continuation of application No. 10/375,780, filed on Feb. 27, 2003, now Pat. No. 7,115,140, which is a continuation of application No. 09/711,034, filed on Nov. 13, 2000, which is a continuation of application No. 08/591,506, filed as application No. PCT/IB95/00492 on Jun. 6, 1995, now Pat. No. 6,187,013.

(30) Foreign Application Priority Data

Jun. 6, 1994 (DK) ...................................... 0638/94

(51) Int. Cl.
*A61F 2/06* (2013.01)

(52) U.S. Cl.
USPC ...................................................... 623/1.11

(58) Field of Classification Search
USPC ......................................................... 623/1.11
See application file for complete search history.

(56) References Cited

U.S. PATENT DOCUMENTS

| 4,733,665 A | 3/1988 | Palmaz |
| 4,762,128 A | 8/1988 | Rosenbluth |
| 4,800,882 A | 1/1989 | Gianturco |
| 4,878,906 A | 11/1989 | Lindemann et al. |
| 4,886,062 A | 12/1989 | Wiktor |
| 4,906,244 A | 3/1990 | Pinchuk et al. |
| 4,913,701 A | 4/1990 | Tower |

(Continued)

FOREIGN PATENT DOCUMENTS

| EP | 0312852 | 4/1989 |
| EP | 0 442 657 | 8/1991 |

(Continued)

OTHER PUBLICATIONS

Cook Cardiology, *Cook Manuals*, GR Flex-Stent Training Manual, N.B. (1997).

(Continued)

*Primary Examiner* — Darwin Erezo
(74) *Attorney, Agent, or Firm* — Hoffmann & Baron, LLP

(57) ABSTRACT

A method is provided for mounting a stent onto a catheter system. The method includes selecting a catheter having a first end where the first end includes an inflatable portion thereat. An adhesive bond is formed between the stent and the inflatable portion causing the stent to adhere to the inflatable portion. The formed adhesive bond is such that upon release of the stent from the inflatable portion upon inflation, the adhesive bond remains with the inflatable portion.

4 Claims, 5 Drawing Sheets

(56) References Cited

U.S. PATENT DOCUMENTS

| | | |
|---|---|---|
| 4,969,458 A | 11/1990 | Wiktor |
| 5,026,377 A | 6/1991 | Burton et al. |
| 5,037,427 A | 8/1991 | Harada et al. |
| 5,100,429 A | 3/1992 | Sinofsky et al. |
| 5,195,984 A | 3/1993 | Schatz |
| 5,201,901 A | 4/1993 | Harada et al. |
| 5,242,399 A | 9/1993 | Lau et al. |
| 5,290,306 A | 3/1994 | Trotta et al. |
| 5,292,321 A | 3/1994 | Lee |
| 5,292,331 A | 3/1994 | Boneau |
| 5,342,307 A | 8/1994 | Euteneuer et al. |
| 5,484,444 A | 1/1996 | Braunschweiler et al. |
| 5,484,449 A | 1/1996 | Amundson et al. |
| 5,505,699 A | 4/1996 | Forman et al. |
| 5,569,295 A | 10/1996 | Lam |
| 5,603,721 A | 2/1997 | Lam et al. |
| 5,643,278 A | 7/1997 | Wijay |
| 5,693,085 A | 12/1997 | Buirge et al. |
| 5,836,965 A | 11/1998 | Jendersee et al. |
| 5,976,181 A | 11/1999 | Whelan et al. |
| 6,077,273 A | 6/2000 | Euteneuer et al. |
| 6,159,229 A | 12/2000 | Jendersee et al. |
| 6,309,402 B1 | 10/2001 | Jendersee et al. |

FOREIGN PATENT DOCUMENTS

| | | |
|---|---|---|
| JP | 5-038367 | 2/1993 |
| JP | 6-86827 | 3/1994 |
| WO | WO 91/17789 | 11/1991 |
| WO | WO 94/05364 | 3/1994 |
| WO | WO 00/53123 | 9/2000 |

OTHER PUBLICATIONS

Cook, Inc., *Premarket Approval of Gianturco-Roubin Flex-Stent Coronary Stent*, Dept. of Health and Human Services, Food and Drug Administration, Docket No. 93M-0212 (1990) [58 FR 39217 (Jul. 22, 1993)].

Minutes of Meeting, *Circulatory System Devices Panel*, Department of Health and Human Services, Food and Drug Administration, Washington D.C. May 11, 1992.

Memorandum Opinion, May 31, 2000, *Medtronic Ave, Inc.*, v. *Cordis Corporation*, U.S. District Court for the District of Delaware, C.A. No. 99-833-SLR.

SCIMED Opposition to EP 787,020 B1 filed Apr. 30, 2003.

FIG.6B
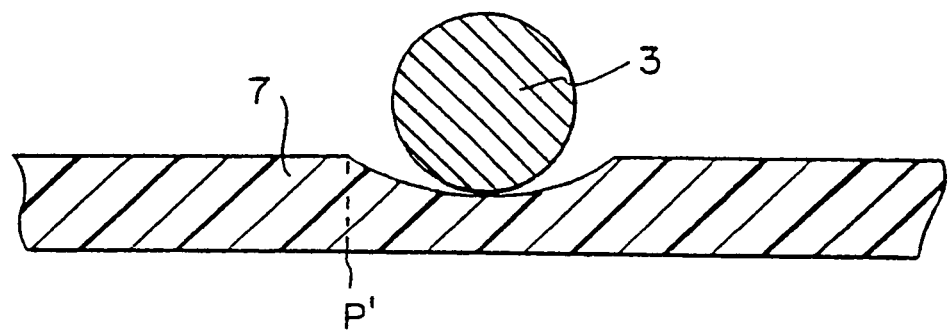
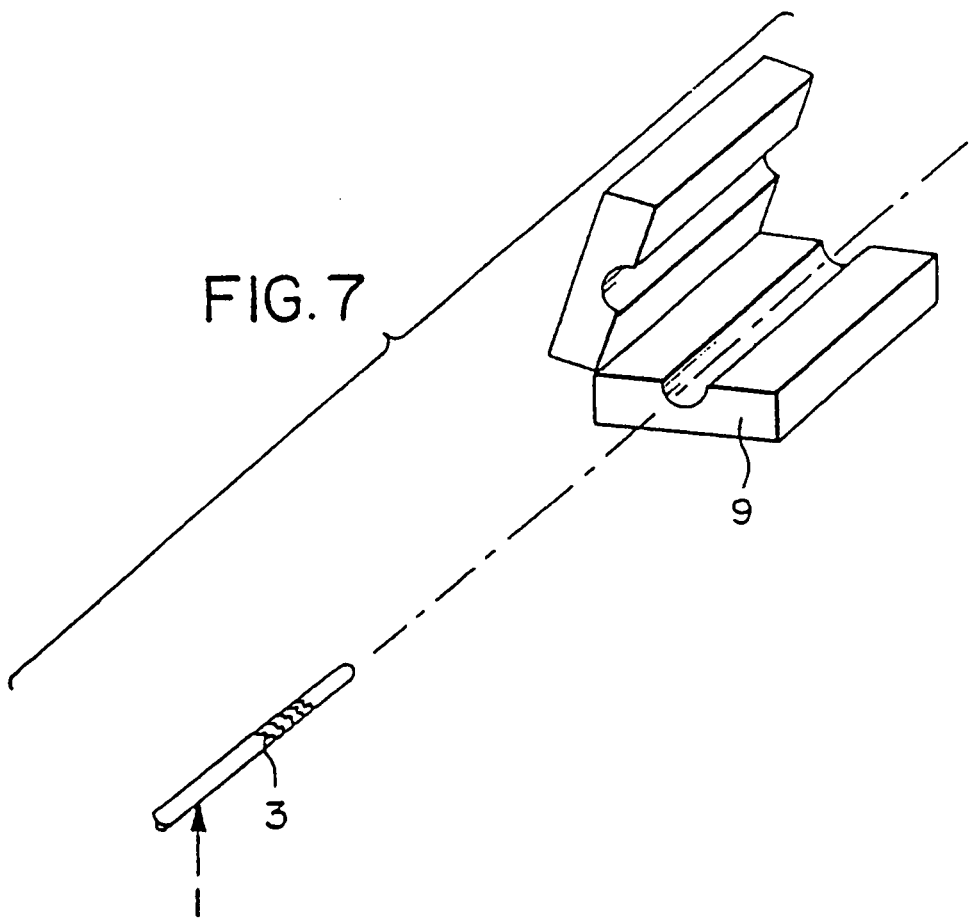
FIG.7

CATHETER WITH STENT AND METHOD FOR THE PRODUCTION OF A CATHETER WITH STENT

CROSS-REFERENCE TO RELATED APPLICATIONS

This application is a continuation of and claims priority to U.S. Pat. No. 7,115,140 (was Ser. No. 10/375,780 filed on Feb. 27, 2003), which is a continuation of Ser. No. 09/711,034, filed on Nov. 13, 2000, which is a continuation of Ser. No. 08/591,506, filed on Aug 19, 1996, now U.S. Pat. No. 6,187,013, which is a §371 of PCT/IB95/00492, filed on Jun. 6, 1995, which claims priority to Danish Application No. 0638/94, filed on Jun. 6, 1994, which are all incorporated herein by reference.

The present invention relates to a catheter system for introducing and implanting a stent and comprising a catheter having at its one end an expandable portion, at its opposite end elements intended for communication with means for expanding the expandable portion, and a stent made of a material to which a permanent deformation for maintaining an enlarged transverse dimension is imparted when the catheter is expanded, said stent being arranged around the expandable portion of the catheter and releasably fixed to the catheter to prevent movement of the stent during insertion.

In case of partially occluded blood vessels, e.g. due to arteriosclerosis, it was previously necessary to perform surgery directly at the site of occlusion to cure a patient suffering from this kind of disorder. Such partial occlusion may be dilated by introducing a catheter with an expandable portion into the blood vessel and expanding the expandable catheter portion in the partially occluded area. However, this is not always sufficient since the partially occluded portion may be reestablished or relapse to its partially occluded state. In recent years it has become increasingly common to treat such cases by implantation of a stent (an endoprosthesis) into the partially occluded portion of a blood vessel. Following implantation, the stent influences the blood vessel to the effect that the latter stays dilated. In most instances, the patient will avoid more severe consequences of such disorder in the future.

Various types of catheters with expandable portions are available. A first type is designed with a portion which, under the influence of pressure, is expanded by elastic deformation of the expandable portion. This type is most often designated balloon catheters. A particular embodiment of such catheter is disclosed in UK 156674. This catheter comprises a reinforcement web in its expandable portion, said reinforcement web having a rhomb pattern. Expansion of the expandable portion of such catheter entails simultaneous reduction of the length of said portion.

A second type of catheter is made of a substantially non-elastomeric material and provided with elements which are, in the unexpanded state of the catheter, for instance rolled/folded around the remaining catheter assembly. Pressure influences will cause the expandable portions to unfold.

Stents, too, are available in various embodiments. Distinction is made between pressure-expandable stents and auto-expandable stents. The stent type relevant to the present invention is the pressure-expandable one to which pressure influences from the catheter imparts a permanent deformation until the desired introduction diameter has been reached. An example of such stent is known from EP 312852. The stent disclosed therein is a stent made from a coherent thread.

The implantation of such stent is effected by means of a catheter provided with an expandable portion onto which the stent is arranged. The catheter with the stent is introduced e.g. in the groin region if the stent is to be lodged in a blood vessel in a leg, and it is guided under x-ray monitoring to the partially occluded site whereupon means connected to the catheter applies a pressure to said catheter and the expandable catheter portion urges the stent out towards the blood vessel wall. The pressure is subsequently reduced and the catheter may then be withdrawn from the blood vessel whereas the stent in its expanded state remains in the blood vessel portion which requires treatment. The operation is relatively simple compared to the surgical intervention otherwise required at the partially occluded site and thus it is desirable in many situations.

The use of balloon catheters to deliver various types of stents has become widely used in the medical field. Such relatively non-invasive techniques offer many advantages to both patient and surgeon. Notwithstanding the advances made in this area, several problems still exist with respect to preventing the stent from unwanted movement on the uninflated balloon during insertion, placement, and final positioning of the stent prior to expansion and full deployment. Often the stent moves relative to the balloon during its negotiation through tortuous vessels and becomes off-centered on the inflatable balloon, such that it incompletely or improperly expands. In a worst case scenario, the balloon may move such that its expansion and proper positioning are not possible. For example, EP-A-0442657 discloses a catheter system of the type described above where the stent is arranged around the expandable catheter portion and where collars or sleeves are mounted on the catheter serving only to secure the stent at its end portions.

Owing to its collars, this known catheter system has a relatively large diameter. Moreover the catheter system is associated with the drawback that there is a risk of the stent moving away from the catheter surface during introduction of the catheter system through the small bending radii of a blood vessel, thereby causing damage to the blood vessel.

U.S. Pat. No. 4,950,227 discloses a similar system wherein, however, an alternative stent embodiment is used, viz. the so-called "knitted stent", whereby the risk of the stent moving away from the catheter surface is reduced but not completely eliminated. Like the above-described catheter system, however, the catheter system known from this U.S. patent is disadvantageous, too, due to the use of collars for mechanical securing of the stent and the ensuing increased outer diameter.

Efforts to solve the unwanted movement of the stent during insertion have included using adhesive to bond the stent to the balloon. For example, U.S. Pat. No. 5,100,429 employs a photo-degradable adhesive to bond the balloon to the stent. Light is then used to degrade the adhesive once the stent is inserted into the body. In this disclosure the stent used is of the type which is rolled around the catheter assembly which means that the aggregate system has a relatively large cross section at this point. Thereby the fields of application of the system are restricted. Moreover, practice has shown that there will always be residues of adhesive left on the implanted stent, which residue is to be degraded so as not to cause occlusion of the blood vessel. Thereby the implantation is rendered more difficult and the system presupposes particular adhesives, e.g. a light-degradable adhesive, and means, e.g. a light source, in connection with the catheter to degrade the adhesive.

The fact that thus the known catheter systems which incorporated stents have relatively large transverse dimensions due to their having portions which overlap the stent ends or optionally the entire stent, or due to the stent being rolled around the catheter assembly, the fields of application of such catheter systems are restricted. Moreover, there is a certain risk associated with the known systems that adhesive residues adhere to the implanted stent.

It is therefore one object of the invention to provide a catheter system of the type which in a simple manner ensures reliable securing of the stent against the catheter and simultaneously allows such catheter system to be designed with a substantially reduced transverse dimension compared to the prior art and without the risk of adhesive residues or catheter materials sticking to the implanted stent.

This is obtained with a catheter system which is characterized in that the stent is adhesively connected to the expandable catheter portion with adhesive forces between stent and support which are less powerful than the shear forces applied by the expandable portion which influence the adhesive connection when this portion is expanded. The stent is releasably connected at the bondline to the expandable portion of the catheter by adhesion forces which are weaker than the shear forces created at the bondline when the expandable portion is expanded and whereby said bondline adhesively fails at the stent surface, i.e. stent/adhesive interface, during expansion to release said stent. The term "adhesively fails" as used herein is meant to indicate failure at the interface and not in the matrix of the adhesive per se.

Thus, the adhesive communication may be formed by use of a suitable adhesive or through softening of the catheter surface and subsequent positioning of the stent thereon.

According to a particularly suitable embodiment of the invention, the stent is at least partially depressed into the catheter surface in the expandable catheter portion in its unexpanded state. Thereby the further advantage is obtained that the depression formed by depressing the stent into the catheter surface prevents axial displacement of the stent relative to the catheter and the transverse dimension of the catheter system is further reduced.

The idea of using adhesives to bond the stent to the balloon has inherent problems with respect to adhesive residue which may be left behind once the bond is broken. Such residue, even if biodegradable over time, may present problems and cause blockage in smaller vessels, as well as other side effects.

The present invention seeks to offer a solution to securing the stent to the inflatable portion of the catheter, such that a releasable bond is formed without the risk of adhesive residue. In one embodiment, the bond is formed by the same material as the inflatable portion of the balloon. This can be achieved by softening the exterior wall of the balloon and depressing the stent into the stent into the softened, inflatable wall and allowing the softened material to adhere to the stent. The formation of such a bond is, in effect, a hot-melt joint. This bond can be effected with a number of different types of stents, including wire stents or cage stents, as well as porous tubular stents. The bond joint may occur at each point of contact between the stent and the balloon surface, or it may be formed at preselected, spaced apart contact points.

In another embodiment, a separate adhesive material, being the same or different from the material comprising the balloon wall, may be employed. In this case, however, it is necessary that the adhesive material have a modulus of elasticity which is substantially similar to the modulus of the balloon. This is to allow the adhesive to remain stationary relative to the balloon during expansion of the balloon and release itself from the stent without leaving residue. While it is not necessary that the moduli between the adhesive and the inflatable portion (balloon) be exactly the same, it is preferred that the degree of difference between the adhesive modulus of elasticity and the stent modulus of elasticity be maximized and the differential between the modulus of the inflatable balloon and that of the adhesive be minimized.

This requirement is to prevent the adhesive from shearing from the balloon during expansion and remaining on the stent once it is deployed. If the adhesive has a modulus of expansion which is much closer to the modulus of the balloon than of the stent, the adhesive will have a tendency to remain stationary with respect to the balloon but will move at the bondline joint with respect to the stent. This can further be illustrated with respect to FIGS. 8A and 8B. At a given contact surface between the stent and the wall surface of the balloon, various contact points can be identified. During expansion, all of these points begin to move nearly simultaneously in a shear direction. If the modulus of elasticity of the adhesive is such that the adhesive points do not move relative to the balloon, i.e., expand with the balloon, the shear forces will not lift the adhesive from the balloon surface and the adhesive will remain attached to the wall. However, at the bondline interface between the stent and the adhesive, the points of contact are now moving relative to each other and the bond will then be overcome by the shear forces and be released from the stent, thereby freeing the stent from adhesive and permitting deployment of the stent into the vessel without adhesive residue. If the differences between the moduli of the stent and the adhesive are great enough, the release of the bond between these components can easily be effectuated, since all the points of contact will substantially move simultaneously. This principle can be illustrated in simplified fashion through the use of an adhesive bandage on the skin. If the adhesive bandage is removed by peeling very slowly, it is difficult and painful to remove. However, if the adhesive bandage is elastomeric and can be stretched, it can be easily removed by stretching its ends in opposite directions, thereby applying shear forces at opposite ends. In this manner, the bandage lifts very easily, without pulling the skin and with a nominal amount of force. This is because all the points of adhesive contact are moving relative to the skin which remains stationary.

The present invention seeks to take advantage of such principles by providing a catheter system which includes a catheter member having an inflatable portion and a stent member which is capable of permanent deformation when expanded and which is releasably attached to said inflatable portion by a bond, whereby upon inflation of said inflatable portion, the bond is released from the stent to permit deployment of the stent member into the body.

In the present invention the incorporation of additional elements, e.g. collars, for mechanically securing the end portions of the stent or optionally the entire stent assembly is avoided and the entire catheter system may thus be constructed with substantially smaller transverse dimensions, i.e. diameter, than the prior art, which is of considerable importance when introduction into the patient of the catheter with its integral stent is effected through an introducer sheath, thereby also making it possible to subsequently select an introducer sheath with a smaller diameter. The size of the introducer sheath is crucial to the expediency of the patient's recovery and discharge from the hospital following treatment. As a consequence of this reduction of the required hospitalization period, the option that a narrower introducer sheath may be used both contributes to the well being of the patient and rationalizes the operation of the hospital.

In one embodiment, the present invention includes a catheter system for introducing and implanting a stent in a body, said system including a catheter member having first and second ends, said first end having an inflatable portion, a lumen in fluid communication with said inflatable portion and said second end to provide means for inflating said inflatable portion; and an expandable stent member capable of permanent deformation when expanded, at least a portion of said stent member being attached to said inflatable portion by a bond, whereby upon inflation of said inflatable portion said bond is released from said stent member to permit deployment of said stent member and removal of said catheter member.

The bond may comprise an adhesive which must be selected from among those which has a modulus of elasticity such that upon expansion of the catheter's expandable or inflatable portion, the bond, i.e., adhesive connection, between the inflatable portion (balloon) and the adhesive itself, is influenced or subjected to a weaker force at the balloon/adhesive bondline than the force which is influencing the stent/adhesive bondline. By selecting such an adhesive for this purpose, it is ensured that the adhesive will remain on the catheter surface during implantation of the stent. The selection of an appropriate adhesive can be made on the basis of the modulus of elasticity. By selecting an adhesive with a modulus of elasticity which more closely approximates the modulus of elasticity of the inflatable portion of the catheter, very little shear force will be placed on the balloon/adhesive bondline (interface) during balloon expansion. A relatively higher shear force will be experienced, however, at the stent/adhesive bondline due to the large differences in the modulus of elasticity between the stent and the adhesive per se.

Although the adhesive may be selected from a material which is different from that of the balloon, it is preferred to form the adhesive bond using the balloon material per se. This accomplished by softening the balloon material, depressing the stent into the softened area and allowing the balloon material to adhere at the points of contact. As previously described, this adhesive connection is essentially a hot-melt joint whereby the stent releasably bonds to the balloon. In this instance, since no separate or additional adhesive is used to form the bond, there is no residue which remains once the balloon expansion releases the stent. In this embodiment, the modulus of elasticity of the balloon and the adhesive are substantially identical since they are the same material. Their moduli are significantly smaller than that of the stent. Thus, the differential between the stent and balloon moduli are maximized to produce the desired result.

The stent is advantageously depressed into the catheter surface in the expandable portion in a depth corresponding to from one twentieth to one half of the stent material thickness and more advantageously from one tenth to one third.

Moreover the invention relates to a method of producing a catheter system for the introduction and implantation of a stent which catheter system comprises a catheter with an expandable portion at its first end and a plastically deformable stent arranged around the expandable catheter portion.

The method includes the steps of positioning the stent around the expandable catheter portion, softening the surface of the expandable catheter and applying pressure to the stent to obtain at least partial depression into the catheter surface.

A particularly simple way of doing this is by arranging the catheter carrying the stent on the inflatable catheter portion in a device which encloses the stent and introducing a fluid under pressure into the catheter through the elements intended therefor at the opposite end of the catheter so as to expand the expandable catheter portion and urge the stent towards the inside of the device whereby the stent is depressed into the catheter surface.

The fluid pressure in the catheter is then subsequently reduced whereby the cross section of the expandable catheter portion is concurrently reduced and the catheter bearing the depressed stent may be removed from the device.

The method described above is thus both simple and efficient for the production of catheters according to the invention where the stent is depressed into the catheter surface.

In another embodiment, a separate adhesive is used to join the stent and inflatable portion. The adhesive is selected to form a bond which releases only at the stent/adhesive interface and not at the balloon/adhesive interface.

The softening of the catheter surface may for instance be effected by application of a solvent. However, it is particularly advantageous to soften the catheter surface by heating, this process being easily controllable. When the softened catheter surface resumes its stable state, the stent will moreover adhere to the catheter material which contributes further to the securing of the stent during introduction of the catheter into a blood vessel. When an adhesive is applied the catheter surface may be constituted of such an adhesive layer.

The invention will now be described in further detail with reference to the drawings, wherein FIG. 1 is an overall view of the catheter system according to the invention.

FIGS. 6A and 6B are more detailed sectional views through a section of a catheter where a stent is depressed into the catheter surface and shown in the unexpanded and expanded states, respectively.

FIG. 7 is a schematical view of a useful device for bonding the inflatable portion of the catheter to the stent.

Figure 1:
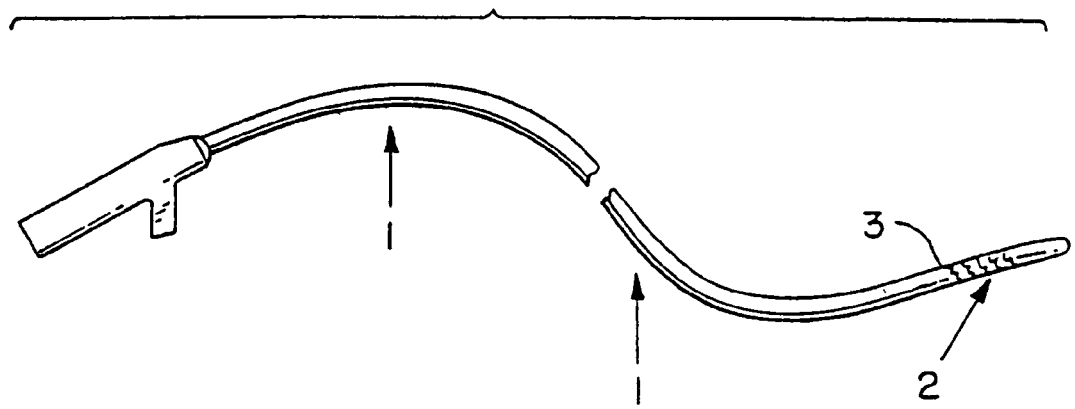

FIG. 1 shows one embodiment of the catheter system according to the invention. The catheter system comprises a catheter 1 with an expandable portion 2 at its first end, a stent 3 arranged around the expandable catheter portion, and elements at the opposite end of the catheter intended for communication with means for expanding the expandable portion 2.

Figure 2:
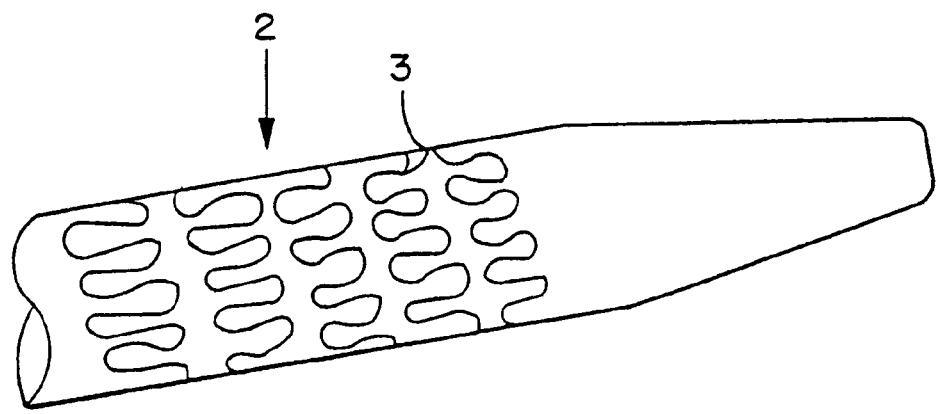
FIG. 2 is a more detailed view of the expandable portion of a catheter in its unexpanded state and having a stent secured thereto.

FIG. 2 is a more detailed view of the stent 3. The stent is made of a coherent metal thread. This thread is curved and thus it appears as a band coiled around the catheter whereby a tubular stent 3 is formed.

Figure 3:
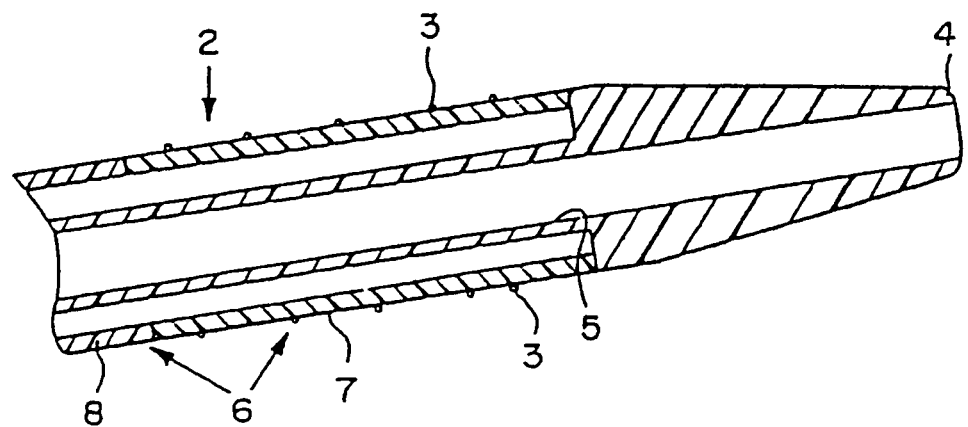
FIG. 3 is a sectional view through a catheter in its longitudinal direction and at the expandable portion.

FIG. 3 shows the construction of a catheter 1 which in a manner known per se is provided with an expandable portion. Herein, the introduction end 4 of the catheter and an inner tubular member 5 is formed integrally. The introduction end 4 is open between its tip and the tubular member 5. Hereby a guide wire (not shown) may be used for the introduction of the catheter into a blood vessel. Around and at a distance from the inner tubular member 5 an outer tubular member 6 is arranged. The outer tubular member is made partly of an elastically deformable material 7, preferably a thermoplastic elastomer, partly of a non-deformable material 8.

Figure 4:
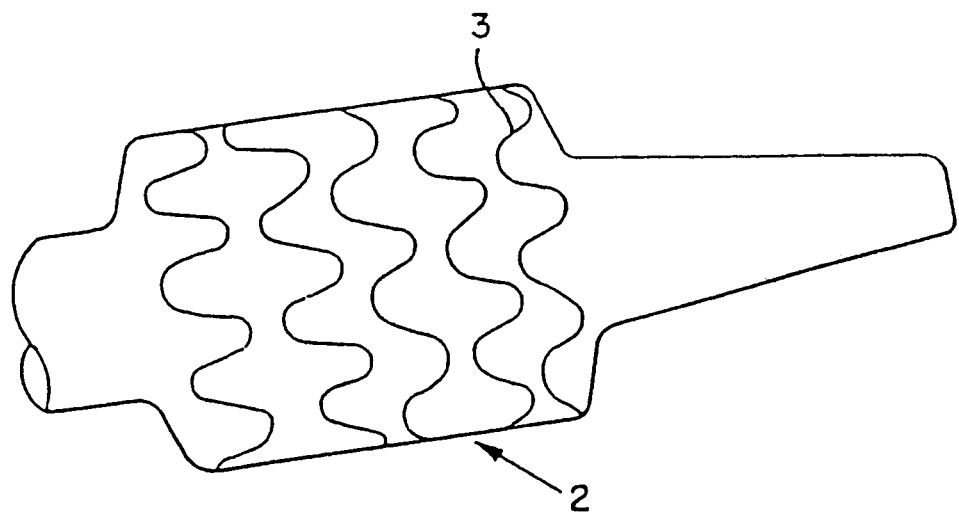
FIG. 4 shows the catheter and the stent corresponding to FIG. 2 where, however, the catheter is expanded.
Figure 5:
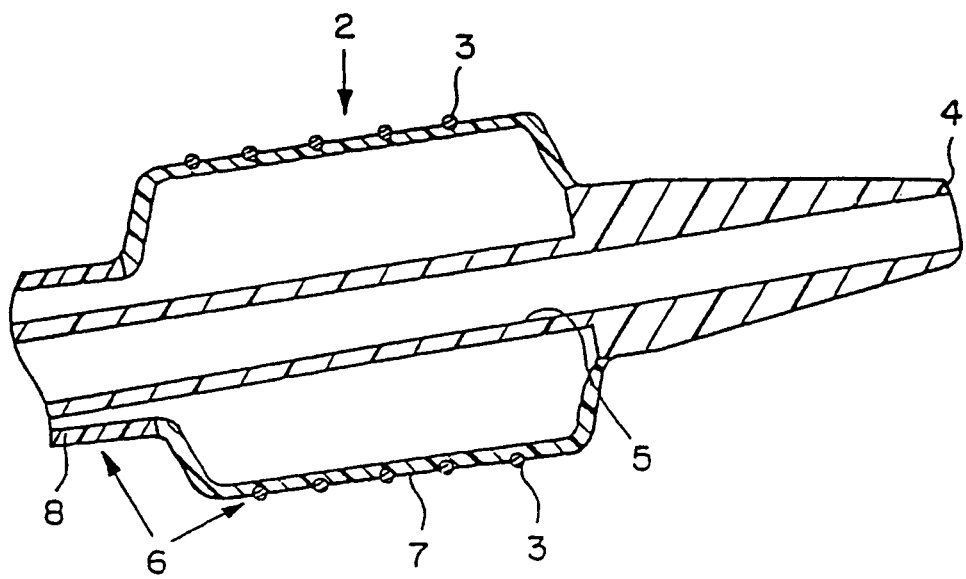
FIG. 5 is a sectional view through a catheter at its expandable portion where the catheter is expanded.

When the elements at the opposite end of the catheter are connected to e.g. a fluid pressure source, fluid under pressure will enter the space between the inner and the outer tubular member and thereby cause the elastomeric material 7 to be extended and the cross section of the catheter to be increases as will appear from FIG. 4. At the same time the stent material is deformed as the curves are moved away from each other. FIG. 5 shows a section through a catheter in the state shown in FIG. 4.

Figure 6A:
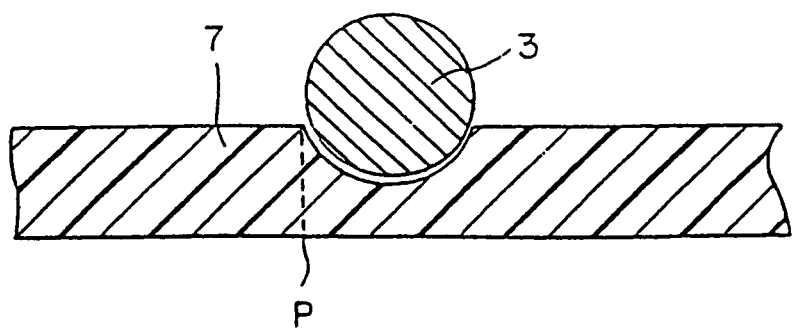

FIG. 6A shows how the stent 3 is depressed into the surface of the elastically deformable catheter material 7 in an unexpanded state of the catheter. Since the catheter material 7 is extended under the influence of pressure, the partially circular depression formed in the catheter surface and shown in FIG. 6A will be so deformed that the contact face between catheter and stent is reduced as indicated in FIG. 6B. It is outlined schematically that a point P, which in an unexpanded state is situated immediately adjacent to the stent thread, is situated a distance from the stent threat at P' in the expanded state of the catheter. Thus, partial displacement of the contact elements is effected relative to the stent and the catheter surface, respectively. Discontinuation of the pressure influence and the ensuing reduction of the catheter cross section leaves the stent in its expanded state as will appear from FIG. 4.

FIG. 7 shows an end portion of a catheter where a stent is arranged around an expandable catheter portion, while the stent is not yet depressed into the catheter surface. According to a preferred embodiment of the method according to the invention the catheter 1 and the stent 3 are introduced into a heating device 9. The temperature in the heating device is maintained at from 50° C. to 250° C., preferably about 150° C., and after a certain period of time depending on the actual temperature, the catheter surface will be softened. The elements at the opposite end of the catheter are connected to e.g. a fluid pressure source and fluid under pressure causes the expandable portion of the catheter to expand and to urge the stent towards the inner wall of the device whereby the stent is depressed into the catheter surface. When the pressure is reduced, the cross section of the catheter will be reduced whereupon the catheter and the stent may be removed from the device. When the catheter surface is softened and the stent subsequently depressed into the surface, an adhesive connection between catheter and stent is also obtained which contributes further to secure that the stent is fixed relative to the catheter during introduction into a blood vessel. The expansion occurring during mounting of the stent in the catheter surface is of a range which causes only elastic deformation thereof. Thus, any expansion of the stent during this mounting process reverses itself to the non-expanded state once the thus formed catheter system is removed from the fixture.

Figure 8A:
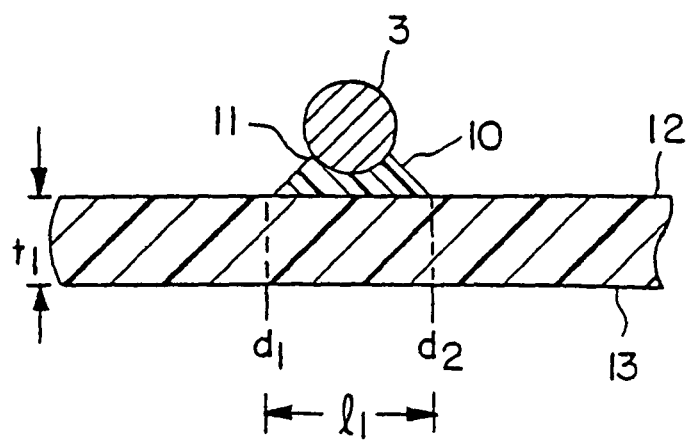
FIGS. 8A and 8B are schematic sectional views taken longitudinally through a catheter at its expandable portion showing the use of a separate adhesive bonding the stent to the balloon.
Figure 8B:
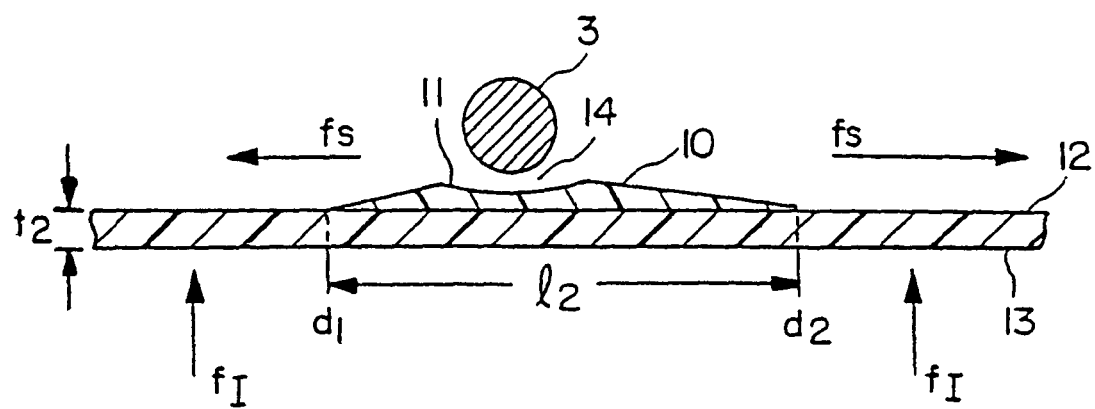

FIG. 8A shows the unexpanded balloon and FIG. 8B shows the expanded balloon with the inflation forces $f_r$ and shear forces shown with directional arrows at the bondline interface between the adhesive and stent. FIG. 8A represents an embodiment of the present invention showing the use of a separate adhesive in the form of a fillet 10 which defines a bondline at interface 11 between stent 3 and fillet 10. The adhesive forms the connection between stent 3 and the external surface of balloon 12. In this view, the balloon is in an unexpanded state, i.e. deflated. The external surface 12 and the internal surface 13 of the balloon define a thickness $t_1$ which is the thickness of the inflatable balloon. Two points are marked on the balloon surface as $d_1$ and $d_2$. The distance between these two points, which are positioned at the corners of the adhesive fillet 10, is defined as $l_1$ indicating the starting length between the two points. During inflation as depicted in FIG. 8B, inflationary force $f_r$ is applied to the internal surface 13 of the balloon such that expansion is initiated. Simultaneously, as the balloon stretches, shear forces $f_s$ exist at the bondlines of the adhesive connection. The elastomeric adhesive forming fillet 10 has been chosen to have an elastic modulus such that it expands along with the balloon. During the expansion, the thickness of the balloon is diminished to $t_2$ (less than $t_1$) and the shear forces which act throughout the adhesive connection separate at bondline 11 causing the release of the stent from the adhesive and leaving a gap 14 such that the balloon can be removed to allow permanent fixture of the stent 3 in the body. No adhesive residue remains on the stent during the expansion of the balloon. There is less movement between the adhesive and the balloon interface than between the stent and adhesive interface, thereby indicating that less force is required at bondline 11 to release the stent since adhesive 10 and stent 3 were in movement relative to each other during the expansion process.

The material from which the expandable portion of the catheter is made may be chosen from a number of thermoplastic elastomeric polymers which are capable of being inflated. Preferably, however, the expandable balloon is made from polyurethane.

The balloon may take a number of configurations and shapes designed to perform in various ways. Additionally, reinforcement and/or expansion control fibers may be provided to the balloon. Generally, these fibers are embedded in the matrix of the balloon in a helical pattern such that they will prevent expansion beyond a pre-specified limit. These fibers are generally selected from a non-elastomeric thermoplastic material such as polyethylene or polyethylene terephthalate. One example of such a reinforced balloon is described in U.K. Patent No. 1,566,674 whereby a reinforcement web is embedded in the expandable balloon. In the balloon's inflated state, the reinforcement web has a rhomb or helical configuration where one rhomb axis is substantially parallel with the catheter axis to which the balloon is attached. Expansion of the expandable catheter portion causes the rhombs to change their axis length such that in the uninflated (unloaded) state, the length of the second transverse axis in its fully expanded state will be increased.

This means that the length of the expandable catheter portion is reduced, i.e. that an axial movement occurs during expansion whereby the stent length is reduced corresponding to the length reduction of the expandable catheter portion, whereby the release of the stent from the catheter is further promoted. This expansion also contributes to the partial displacement of the contact faces as explained above in connection with FIGS. 6A and 6B. However, other catheters will also be suitable for use in connection with the catheter system according to the invention. Moreover, it is also possible to use all types of balloon-expandable stents.

What is claimed:

1. A method for mounting a stent onto a catheter system, the method comprising:
    selecting a catheter having a first end including an inflatable portion; and
    forming an adhesive bond between the stent and the inflatable portion causing the stent to adhere to the inflatable portion,
    said formed adhesive bond being such that upon release of said stent from the inflatable portion said adhesive bond remains with the inflatable portion.

2. The method according to claim 1, wherein the adhesive connection comprises adhesive forces between the stent and the inflatable portion which are less powerful than shear forces applied by the inflatable portion such that the stent is releasably attached to the inflatable portion.

3. The method according to claim 1, wherein the catheter is a balloon catheter and the stent is formed of one or more metal threads or an expandable tubular member with perforations.

4. The method according to claim 1, wherein the inflatable portion is made up of a elastically deformable material.

\* \* \* \* \*